(12) United States Patent
Druliner et al.

(10) Patent No.: US 6,191,311 B1
(45) Date of Patent: Feb. 20, 2001

(54) HYDROPEROXIDE DECOMPOSITION PROCESSES

(75) Inventors: Joe Douglas Druliner; Norman Herron, both of Newark, DE (US)

(73) Assignee: E. I. du Pont de Nemours and Company, Wilmington, DE (US)

( * ) Notice: Under 35 U.S.C. 154(b), the term of this patent shall be extended for 0 days.

(21) Appl. No.: 09/242,844

(22) PCT Filed: Sep. 2, 1997

(86) PCT No.: PCT/US97/15332

§ 371 Date: Feb. 25, 1999

§ 102(e) Date: Feb. 25, 1999

(87) PCT Pub. No.: WO98/09931

PCT Pub. Date: Mar. 12, 1998

Related U.S. Application Data
(60) Provisional application No. 60/025,368, filed on Sep. 3, 1996.

(51) Int. Cl.[7] .................................................. C07C 45/53
(52) U.S. Cl. ........................... 568/342; 568/835; 568/922
(58) Field of Search ................................ 568/909.8, 395, 568/922, 342, 311, 385, 835, 360, 798

(56) References Cited

U.S. PATENT DOCUMENTS

| 4,326,084 | 4/1982 | Druliner et al. ...................... 568/360 |
| 4,503,257 | 3/1985 | Druliner et al. ...................... 568/342 |
| 4,895,680 | 1/1990 | Ellis, Jr. et al. .................. 260/410.9 |
| 4,895,682 | 1/1990 | Ellis, Jr. et al. .................. 260/410.9 |
| 5,298,665 | 3/1994 | Janssen et al. ....................... 568/342 |
| 5,414,163 | 5/1995 | Sanderson et al. ............... 568/909.8 |

OTHER PUBLICATIONS

Patent Abstracts of Japan, vol. 096, No. 009, Sep. 30, 1996. (JP 08 119892, May 14, 1996).
Chemical Abstracts, vol. 75, No. 12, Sep. 20, 1971, #78798j.

*Primary Examiner*—Sreeni Padmanabhan

(57) ABSTRACT

An improved process for decomposing alkyl or aromatic hydroperoxides to form a decomposition reaction mixture containing the corresponding alcohol and ketone. The improvement relates to decomposing the hydroperoxide by contacting the hydroperoxide with a catalytic amount of a heterogeneous catalyst of Nb or Hf hydroxide or oxide. The improvement also relates to decomposing a secondary hydroperoxide by contacting the secondary hydroperoxide with a catalytic amount of a heterogeneous catalyst of Zr or Ti hydroxide or oxide. The catalysts may optionally be supported on $SiO_2$, $Al_2O_3$, carbon or $TiO_2$.

10 Claims, No Drawings

HYDROPEROXIDE DECOMPOSITION PROCESSES

This is the U.S. National Stage application of PCT/U.S. Pat. No. 97/15,332, filed Sep. 2, 1997, and this application claims the benefit of provisional application No. 60/025,368, Sep. 3, 1996.

FIELD OF THE INVENTION

This invention relates to improved catalytic processes for decomposing alkyl or aromatic hydroperoxide to form a mixture containing the corresponding alcohol and ketone.

BACKGROUND OF THE INVENTION

Industrial processes for the production of mixtures of cyclohexanol and cyclohexanone from cyclohexane are currently of considerable commercial significance and are well described in the patent literature. In accordance with typical industrial practice, cyclohexane is oxidized to form a reaction mixture containing cyclohexyl hydroperoxide (CHHP). The resulting CHHP is decomposed, optionally in the presence of a catalyst, to form a reaction mixture containing cyclohexanol and cyclohexanone. In the industry such a mixture is known as a K/A (ketone/alcohol) mixture, and can be readily oxidized to produce adipic acid, which is an important reactant in processes for preparing certain condensation polymers, notably polyamides. Due to the large volumes of adipic acid consumed in these and other processes, improvements in processes for producing adipic acid and its precursors can be used to provide beneficial cost advantages.

Druliner et al., U.S. Pat. No. 4,326,084, disclose an improved catalytic process for oxidizing cyclohexane to form a reaction mixture containing CHHP, and for subsequently decomposing the resulting CHHP to form a mixture containing K and A. The improvement involves the use of certain transition metal complexes of 1,3-bis(2-pyridylimino)isoindolines as catalysts for cyclohexane oxidation and CHHP decomposition. According to this patent, these catalysts demonstrate longer catalyst life, higher CHHP conversion to K and A, operability at lower temperatures (80°–160° C.), and reduced formation of insoluble metal-containing solids, relative to results obtained with certain cobalt(II) fatty acid salts, e.g., cobalt 2-ethylhexanoate.

Druliner et al., U.S. Pat. No. 4,503,257, disclose another improved catalytic process for oxidizing cyclohexane to form a reaction mixture containing CHHP, and for subsequently decomposing the resulting CHHP to form a mixture containing K and A. This improvement involves the use of $Co_3O_4$, $MnO_2$, or $Fe_3O_4$ applied to a suitable solid support as catalysts for cyclohexane oxidation and CHHP decomposition at a temperature from about 80° C. to about 130° C., in the presence of molecular oxygen.

Sanderson et al., U.S. Pat. No. 5,414,163, disclose a process for decomposing tertiary-butyl hydroperoxide in the liquid phase over catalytically effective amounts of unsupported titania, zirconia, or mixtures thereof, to prepare the corresponding alcohol. The preparation of corresponding ketones and the use of secondary hydroperoxides are not disclosed.

Further improvements are needed for hydroperoxide decomposition to K/A mixtures in order to overcome the deficiencies inherent in the prior art. Other objects and advantages of the present invention will become apparent to those skilled in the art upon reference to the detailed description which hereinafter follows.

SUMMARY OF THE INVENTION

In accordance with the present invention, improved processes are provided in which a hydroperoxide or secondary hydroperoxide are decomposed to form a decomposition reaction mixture containing a corresponding alcohol and ketone.

The improvement comprises decomposing a hydroperoxide by contacting a hydroperoxide with a catalytic amount of a heterogenous catalyst selected from the group consisting of Nb and Hf hydroxides or oxides. Preferably, the catalyst is supported on a member selected from the group consisting of $SiO_2$, $Al_2O_3$, carbon, and $TiO_2$.

The improvement also comprises decomposing a secondary hydroperoxide by contacting a secondary hydroperoxide with a catalytic amount of a heterogenous catalyst selected from the group consisting of Zr and Ti hydroxides or oxides. Preferably, the catalyst is supported on a member selected from the group consisting of $SiO_2$, $Al_2O_3$, carbon and $TiO_2$.

DETAILED DESCRIPTION OF THE PREFERRED EMBODIMENTS

The present invention provides improved processes for conducting a hydroperoxide decomposition step in an industrial process in which an alkyl or aromatic compound is oxidized to form a mixture of the corresponding alcohol and ketone. In particular, cyclohexane can be oxidized to form a mixture containing cyclohexanol (A) and cyclohexanone (K). The industrial process involves two steps: first, cyclohexane is oxidized, forming a reaction mixture containing CHHP; second, CHHP is decomposed, forming a mixture containing K and A. As previously mentioned, processes for the oxidation of cyclohexane are well known in the literature and available to those skilled in the art.

By "hydroperoxide" is meant a compound that contains the functional group —OOH attached to a carbon atom.

By "secondary hydroperoxide" is meant a hydroperoxide in which the carbon atom attached to the —OOH group is further connected to only two other carbon atoms.

By "corresponding alcohol" and "corresponding ketone" is meant the alcohol or ketone compound formed by the direct decomposition of the hydroperoxide fragment without the breaking of any carbon-carbon bonds. For example, cyclohexylhydroperoxide is a secondary hydroperoxide, and its corresponding alcohol and ketone would be cyclohexanol and cyclohexanone.

Advantages of the present heterogenous catalytic processes, relative to processes employing homogenous metal catalysts, such as metal salts or metal/ligand mixtures include, longer catalyst life, improved yields of useful products, and the absence of soluble metal compounds. For example, in one extended experiment, soluble niobium was found to be below a detectable level of 100 ppb.

The improved processes can also be used for the decomposition of other alkane or aromatic hydroperoxides, for example, t-butyl hydroperoxide, cyclododecylhydroperoxide and cumene hydroperoxide.

The CHHP decomposition processes can be performed under a wide variety of conditions and in a wide variety of solvents, including CHHP itself. Since CHHP is typically produced industrially as a solution in cyclohexane from catalytic oxidation of cyclohexane, a convenient and preferred solvent for the decomposition process of the invention is cyclohexane. Such a mixture can be used as received from the first step of the cyclohexane oxidation process or after some of the constituents have been removed by known processes such as distillation or aqueous extraction to remove carboxylic acids and other impurities.

The preferred concentration of CHHP in the CHHP decomposition feed mixture can range from about 0.5% by weight to 100% (i.e., neat). In the industrially practiced route, the preferred range is from about 0.5% to about 3% by weight.

Suitable reaction temperatures for the processes of the invention range from about 80° C. to about 170° C. Temperatures from about 110° C. to about 130° C. are typically preferred. Reaction pressures can preferably range from about 69 kPa to about 2760 kPa (10–400 psi) pressure, and pressures from about 276 kPa to about 1380 kPa (40–200 psi) are more preferred. Reaction time varies in inverse relation to reaction temperature, and typically ranges from about 2 to about 30 minutes.

As noted previously, the heterogenous catalysts of the invention include Nb and Hf hydroxides or oxides for all hydroperoxides and Zr and Ti hydroxides or oxides for secondary hydroperoxides, which can optionally be applied to suitable porous solid supports. The metal oxide to catalyst support can vary from about 0.1 to about 50 percent by weight, and is preferably about 1 to about 25 percent. Suitable supports include $SiO_2$ (silica), $Al_2O_3$ (alumina), C (carbon) or $TiO_2$ (titania). $SiO_2$ is a preferred support, and Nb hydroxide or oxide supported on $SiO_2$ is a presently preferred catalyst of the invention. Some of the heterogenous catalysts of the invention can be obtained already prepared from manufacturers, or they can be prepared from suitable starting materials using methods known in the art. These methods can include sol-gel techniques.

The sol-gel technique is a process wherein a free flowing fluid solution, "sol", is first prepared by dissolving suitable precursor materials such as colloids, alkoxides or metal salts in a solvent. The "sol" is then dosed with a reagent to initiate reactive polymerization of the precursor. A typical example is tetraethoxyorthosilicate (TEOS) dissolved in ethanol. Water, with trace acid or base as catalyst to initiate hydrolysis, is added. As polymerization and crosslinking proceeds, the free flowing "sol" increases in viscosity and can eventually set to a rigid "gel". The "gel" consists of a crosslinked network of the desired material which encapsulates the original solvent within its open porous structure. The "gel" may then be dried, typically by either simple heating in a flow of dry air to produce an aerogel or the entrapped solvent my be removed by displacement with a supercritical fluid such as liquid $CO_2$ to produce a xerogel. Final calcination of these dried materials to elevated temperatures (>200° C.) results in products which typically have very porous structures and concomitantly high surface areas.

$SiO_2$, $Al_2O_3$, carbon, or $TiO_2$ catalyst solid supports can be amorphous or crystalline, or a mixture of amorphous and crystalline forms. Selection of an optimal average particle size for the catalyst supports will depend upon such process parameters as reactor residence time and desired reactor flow rates. Generally, the average particle size selected will vary from about 0.005 mm to about 5 mm. Catalysts having a surface area larger than 10 $m^2/g$ are preferred since increased surface area of the catalyst has a direct correlation with increased decomposition rates in batch experiments. Supports having much larger surface areas can also be employed, but inherent brittleness of high-surface area catalysts, and attendant problems in maintaining an acceptable particle size distribution, will establish a practical upper limit upon catalyst support surface area.

The solid catalysts of the invention can be contacted with CHHP by formulation into a catalyst bed, which is arranged to provide intimate contact between catalysts and reactants. Alternatively, catalysts can be slurried with reaction mixtures using techniques known in the art. The process of the invention is suitable for batch or for continuous CHHP decomposition processes.

Adding air or a mixture of air and inert gases to CHHP decomposition mixtures provides higher conversions of process reactants to K and A, since some cyclohexane is oxidized directly to K and A, in addition to K and A being formed by CHHP decomposition. This ancillary process is known as "cyclohexane participation", and is described in detail in Druliner et al., U.S. Pat. No. 4,326,084, the entire contents of which are incorporated herein.

The processes of the present invention are further illustrated by the following non-limiting examples. In the examples, all temperatures are in degrees Celsius and all percentages are by weight unless otherwise indicated.

EXPERIMENTS

Experiment 1

Zirconium hydroxide

Commercially available $Zr(OH)_4$ pellets (MEI, Flemington, N.J.) were heated in a stream of water saturated with nitrogen (30 torr water vapor) at 80° C. for 1 hour. The resulting conditioned material was stored in a tightly capped vial prior to testing for CHHP decomposition.

Experiment 2

Sulfated Zirconium hydroxide

Commercially available sulfated $Zr(OH)_4$ pellets (MEI, Flemington, N.J.) were heated in a stream of water saturated with nitrogen (30 torr water vapor) at 80° C. for 1 hour. The resulting conditioned material was stored in a tightly capped vial prior to testing for CHHP decomposition.

Experiment 3

$Nb_2O_5 \cdot xH_2O$—Niobic Acid 10 g $NbCl_5$ was dissolved into 50 mL dry tetrahydrofuran under nitrogen in a glove box. 5 mL water was added slowly to this solution and an exothermic reaction took place, generating a gelatinous white precipitate. After thoroughly stirring for 30 minutes, the precipitate was collected by filtration, washed with water and tetrahydrofuran and then suction dried. The white solid was then dried in vacuum at 100° C. for 1 hour.

Experiment 4

$ZrO_x(OH)_{4-2x}$ on $SiO_2$ 5 g of silica granules (catalyst support grade, Aldrich, Milwaukee, Wis.) was dried in flowing air (100 mL/min) at 200° C. for 1 hour and taken into a nitrogen filled glove box. The dried silica was slurried into a solution of 1 g $ZrCl_4$ in 25 mL dry acetonitrile for 5 min and then the solvent was removed by evaporation. The dry granules were then heated in flowing air saturated with water vapor (30 torr) in a horizontal tube furnace at 100° C. for 30 min. Finally, the white solid was dried in flowing dry air at 100° C. for 30 min and collected. Analysis revealed a material containing 5.54 wt. % Zr.

Experiment 5

$TiO_x(OH)_{4-2x}$ on $SiO_2$ 5 g of silica granules (catalyst support grade, Aldrich, Milwaukee, Wis.) was dried in flowing air (100 mL/min) at 200° C. for 1 hour and taken into a nitrogen filled glove box. The dried silica was slurried into a solution of 1 g Ti(i-propoxide)$_4$ in 25 mL dry tetrahydrofuran for 5 min, and then the solvent was removed by evaporation. The dry granules were then heated in flowing air saturated with water vapor (30 torr) in a horizontal tube furnace at 100° C. for 30 min. Finally, the white solid was dried in flowing air at 300° C. for 30 min and collected. Analysis revealed a material containing 3.34 wt. % Ti.

Experiment 6

$NbO_x(OH)_{5-2x}$ on $SiO_2$ 5 g of silica granules (catalyst support grade, Aldrich, Milwaukee, Wis.) was dried in flowing air (100 mL/min) at 200° C. for 1 hour and taken into a nitrogen filled glove box. The dried silica was slurried into a solution of 1 g $NbCl_5$ in 25 mL dry acetonitrile for 5 min and then the solvent was removed by evaporation. The dry granules were then heated in flowing air, which had been bubbled through ammonium hydroxide solution (15M), in a horizontal tube furnace at 100° C. for 30 min. Finally, the white solid was dried in flowing air at 300° C. for 30 min and collected. Analysis revealed a material containing 5.40 wt. % Nb.

Experiment 7

$TiO_x(OH)_{4-2x}$ on $\alpha$-$Al_2O_3$ 2 g of α-alumina (Alfa Aesar, Ward Hill, Mass.) was dried in flowing air (100 mL/min) at 200° C. for 1 hour and taken into a nitrogen filled glove box. The dried alumina was slurried into a solution of 1 g Ti(i-propoxide)$_4$ in 25 mL dry tetrahydrofuran for 5 min, and then the solvent was removed by evaporation. The dry granules were then heated in flowing air saturated with water vapor (30 torr) in a horizontal tube furnace at 100° C. for 30 min. Finally the white solid was dried in flowing air at 300° C. for 30 min and collected.

Experiment 8

$Ti_xSi_yO_2$ sol-gel materials 15.2 g tetramethylorthosilicate (Aldrich, Milwaukee, Wis.) was mixed with 50 mL dry methanol in a nitrogen filled glove box. 2.84 g Ti(i-propoxide)$_4$ was added and stirred thoroughly. 25 mL 3M ammonium hydroxide solution was then dripped slowly into the stirred solution which then quickly gelled. Once all of the ammonium hydroxide was added, the gel was aged for 30 min and then washed with water and acetone and suctioned dried. The wet gel was then calcined in flowing air (100 mL/min) at 500° C. for 1 hour generating a granular white solid. This material contained approximately 10 wt. % Ti. Other materials of approximately 1 wt. %, 5 wt. %, and 25 wt. % Ti were prepared in an identical procedure by adjusting the amount of Ti(i-propoxide)$_4$ added in the initial solution.

Experiment 9

$Ti_xSi_yO_2$ sol-gel materials

In a drybox, 28.4 g Ti(i-propoxide)$_4$ (Alfa Aesar, Ward Hill, Mass.) was dissolved in 30 mL isopropanol. To this was added 10.01 g of acetylacetone dissolved in 10 mL isopropanol. The solution was refluxed for 1 hour and then cooled. The solvent was removed in a rotovap. The resulting mixture was then dissolved in 100 mL isopropanol. 22.83 g of tetramethylorthosilicate and 22 mL of isopropanol was added to 12.5 mL of the Ti solution. A solution of 1.2 mL of concentrated HCl in 14.6 g deionized water was added dropwise, then 15 mL more isopropanol was added. After 5 min, 84 mL of isopropanol was added. The yellow solution was stirred for 20 hours at room temperature under a blanket of nitrogen.

The solution was then charged to a 1000 mL autoclave and extracted at 40° C., 3500 psi with liquid $CO_2$ at 10 g/min for 5 hours. The resulting solid product was passed through a 20 mesh sieve, and then calcined at 400° C. under nitrogen for 1 hour, followed by 5 hours at 600° C. under air. The resulting product contained 6.0 wt. % Ti.

Experiment 10

$Zr_xSi_yO_2$ sol-gel materials 2.08 g tetraethylorthosilicate (Aldrich, Milwaukee, Wis.) was mixed with 10 mL dry ethanol under nitrogen using syringe techniques. 1.78 g $ZrOCl_2$ was added and stirred thoroughly. A stoichiometric amount of water was then dripped slowly into the stirred solution which then quickly gelled. Once all of the water was added, the gel was aged for 30 min and then washed with 100 mL water and suctioned dried. The wet gel was then calcined in flowing air (100 mL/min) at 500° C. for 1 hour generating a granular white solid of composition 50 mol % $ZrO_2$, 50 mol % $SiO_2$. Other materials of composition 33:67 and 67:33 mol % $ZrO_2$:$SiO_2$ were prepared in a similiar manner using appropriate ratios of reagents.

Experiment 11

$Zr_xSi_yO_2$ sol-gel materials 2.08 g tetraethylorthosilicate and 1.78 g $ZrOCl_2$ were separately mixed with 5 mL dry ethanol under nitrogen using syringe techniques, and a stoichiometric amount of water was added. The two solutions were then mixed, which quickly gelled. The gel was aged for 30 min and then washed with 100 ml water and suctioned dried. The wet gel was then calcined in flowing air (100 mL/min) at 500° C. for 1 hour generating a granular white solid of composition 50 mol % $ZrO_2$, 50 mol % $SiO_2$. Other materials of composition 33:67 and 67:33 mol % $ZrO_2$:$SiO_2$ were prepared in a similiar manner using appropriate ratios of reagents.

Experiment 12

$NbO_x(OH)_{5-2x}$ sol-gel material a) 3.2 g niobium ethoxide was dissolved into 25 mL sec-butanol. While stirring, 1.8 g water was added and the solution allowed to gel. The gel was aged for 30 mins and then charged to an autoclave and extracted with liquid $CO_2$ in a supercritical method at 200° C. as described in Experiment 9 above. The recovered solid was then calcined at 500° C. in air for 2 hours.

b) An identical material was prepared as in Experiment 12a above except the supercritical drying was carried out at 70° C. instead of 200° C.

Experiment 13

$NbO_x(OH)_{5-2x}$ sol-gel material a) 3.2 g niobium ethoxide was dissolved into 25 mL methanol. While stirring, 1.8 g water was added and the solution allowed to gel. The gel was aged for 30 mins and then charged to an autoclave and extracted with liquid $CO_2$ in a supercritical method at 70° C. as described in Experiment 9 above. The recovered solid was then calcined at 500° C. in air for 2 hours.

b) An identical material was prepared as in Experiment 13a above except the supercritical drying was carried out at 200° C. instead of 70° C.

Experiment 14

$Ti_xSi_yO_2$ sol-gel material 2.08 g tetraethylorthosilicate and 5.68 g titanium iso-propoxide were separately mixed with 10 mL dry ethanol under nitrogen using syringe techniques and a stoichiometric amount of water (1.08 mL) was added. The two solutions were then mixed, which quickly gelled. The gel was aged for 30 mins and then washed with 100 mL water and suction dried. The wet gel was then calcined in flowing air (100 mL/min) at 500° C. for 2 hours giving a white solid of composition 67:33 mol % $TiO_2:SiO_2$.

Experiment 15

$Ti_xSi_yO_2$ sol-gel material 2.08 g tetraethylorthosilicate was mixed with 20 mL dry ethanol under nitrogen using syringe techniques. 5.68 g titanium iso-propoxide was added and stirred thoroughly. A stoichiometric amount of water (1.08 mL) was then dripped slowly into the stirred solution which then quickly gelled. Once all of the water was added, the gel was aged for 30 mins and then washed with 100 mL water and suction dried. The wet gel was then calcined in flowing air (100 mL/min) at 500° C. for 2 hours giving a white solid of composition 67:33 mol % $TiO_2:SiO_2$.

Experiment 16

$TiO_x(OH)_{4-2x}$ 320.67 g of $Ti(OCH_2(CH_3)_2)_4$ (97 wt. %) was slowly poured with rapid stirring into a solution of 800 mL isopropanol, 200 mL water, and a small amount of aqueous ammonia. A white precipitate immediately formed. The solution was stirred an additional 15 minutes after the addition was complete, and was allowed to sit for 5 hr before being stirred briefly to reslurry solids for filtering. The solution was then filtered without washing and dried overnight in vacuo at 70° C. The solids were ground to −40 mesh and dried overnight in air at 109° C.

Experiment 17

$NbO_x(OH)_{4-2x}$ on carbon 5 g of granulated, acid-washed, coconut carbon was dried in flowing nitrogen (100 mL/min) at 150° C. for 1 hour and then taken into a nitrogen filled glove box. The dried carbon was slurried into a solution of 1 g niobium chloride in 40 mL dry acetonitrile. After 5 min stirring, the solution was evaporated to dryness and the recovered granules were heated to 100° C. for 1 hour in flowing air saturated with ammonium hydroxide vapors (by bubbling through 15M ammonium hydroxide solution). The solid was finally dried in flowing air at 300° C. for 1 hour and collected.

Experiment 18

$HfO_x(OH)_{4-2x}$ on silica 5 g of granulated silica (catalyst support grade, Aldrich, Milwaukee, Wis.) was dried in flowing air (100 mL/min) at 200° C. for 1 hour and then taken into a nitrogen filled glove box. The dried silica was slurried into a solution of 1 g hafnium oxychloride in 40 mL dry tetrahydrofuran. After 5 min stirring, the solution was evaporated to dryness and the recovered granules were heated to 100° C. for 1 hour in flowing air saturated with ammonium hydroxide vapors (by bubbling through 15M ammonium hydroxide solution). The solid was finally dried in flowing air at 300° C. for 1 hour and collected.

EXAMPLES

All reactions were run either in batch or continuous reactor mode. Batch reactions were run in stirred 3.5 mL glass vials, sealed with septa and plastic caps. Vials were inserted into a block aluminum heater/stirrer apparatus that holds up to 8 vials. Stirring was done using Teflon®-coated stir bars. Each vial was first charged with 1.5 mL of n-octane solvent, approximately 0.005 or 0.01 g of a given crushed catalyst, a stir bar and the vial was sealed. Vials were stirred and heated for approximately 10 minutes to assure that the desired reaction temperature had been attained. Next, at the start of each example, mL amounts (15 to 75 mL) of a stock solution of CHHP and TCB (1,2,4-trichlorobenzene), GC (gas chromatograph) internal standard, were injected. Stock solutions consisted of mixtures of weighed amounts of TCB (12–15 wt. %) in CHHP. The CHHP sources contained up to 2.0 wt. % of combined cyclohexanol and cyclohexanone. Vials were removed from the aluminum heater/stirrer at the end of a given example. In the case of Examples 1–4 (Table 1), 0.14–0.35 mL of solutions of TPP(triphenylphosphine) in toluene was injected by syringe into each vial, so as to provide an excess of TPP relative to the amount of starting CHHP. Any unreacted CHHP quantitatively reacted with TPP to form 1 equivalent of cyclohexanol and 1 equivalent of TPPO (triphenylphosphine oxide). TPPO was then analyzed for by GC on a 30 m DB-5 capillary column with an internal diameter of 0.53 mm. The liquid phase of the column was comprised of (5 wt. % phenyl) methyl polysiloxane. The column was obtained from J. and W. Scientific, Folsum, Calif.

In Examples 5–12 (Table II) and Examples 22–35 (Table IV), vials were removed from the aluminum heater/stirrer, were allowed to cool to ambient temperature and were then analyzed directly for the amount of CHHP remaining using a 15 m DB-17 capillary column with a 0.32 mm internal diameter. The liquid phase of the column was comprised of (50 wt. % phenyl) methyl polysiloxane. The column was obtained from J. and W. Scientific, Folsum, Calif.

In both GC analyses the amounts of TPPO and CHHP in each solution were calculated using the equations:

wt. % TPPO=(area % TPPO/area % TCB)×wt. % TCB× $R.F._{TPPO}$ wt. % CHHP=(area % CHHP/area % TCB)×wt. % TCB× $R.F._{CHHP}$ $R.F._{TPPO}$ and $R.F._{CHHP}$ (GC response factor for TPPO and CHHP, respectively) were determined from calibration solutions containing known amounts of TPPO, CHHP and TCB, and were calculated from the equations:

$$R.F._{TPPO} = \frac{wt.\% \, TPPO / area \, \% \, TPPO}{wt.\% \, TCB / area \, \% \, TCB}$$

$$R.F._{CHHP} = \frac{wt.\% \, CHHP / area \, \% \, CHHP}{wt.\% \, TCB / area \, \% \, TCB}$$

In batch Examples 5–12 (Table II) and Examples 22–35 (Table IV), the initial concentrations of CHHP in each vial were approximately 1 or 2 wt. %, as shown in the Tables. The GC wt. % CHHP initial and CHHP final numbers are only approximate because the amount of TCB per g solution ratios used in GC calculations were arbitrarily all made equal to 0.25 mg TCB/1 g solution. Also, different TCB/CHHP solutions were used for different sets of reaction vials. Since an unheated sample of 1.5 mL n-octane and 30 mL CHHP/TCB solution was analyzed with each set of CHHP decomposition product vials made from the same CHHP/TCB solution, accurate changes in CHHP/TCB ratios could be calculated.

Examples 13–21 (Table III) were run using a continuous reactor constructed from a 15 in. long, ¼ in. diameter stainless steel tube with valves on top and bottom. A liquid chromatography pump was connected via back pressure regulators to allow pressures to be varied. The reactor effluent, after passing through a back pressure regulator to reduce it to atmospheric pressure, was collected by turning a valve to direct flow to a small tube. The reactor was heated using a split tube furnace. Feed solutions contained approximately 1.5 wt. % A(cyclohexanol), 0.6 wt. % K(cyclohexanone), 1–2 wt. % CHHP and minor amounts of carboxylic acids and water, with the balance being cyclohexane. Approximately 1 g of catalyst, screened to 20–40 mesh, was placed in the reactor for each example. Pressures were set to 50 psig with a liquid feed rate of 1 mL per minute. GC analyses for the amounts of CHHP remaining in each sample were performed using the DB-17 column described above. The exact wt. % TCB present in each feed solution for a given continuous example was not known, but was in the range of approximately 0.1–0.2 wt. %. Samples of feed solution were taken at the same times for each product solution, and both were analyzed for the wt. % CHHP. The percentage decrease in wt. % CHHP for each product sample could thus be calculated.

Examples 1–4 (Table I) give batch % CHHP decomposition results for bulk metal hydroxide catalysts. Examples 5–12 (Table II) give batch % CHHP decomposition results for titanosilicate catalysts prepared by sol-gel techniques. Examples 22–35 (Table IV) give batch % CHHP decomposition results for $Nb_2O_5$, ZrSiO and TiSiO catalysts prepared by sol-gel techniques. Examples 13–21 (Table III) give continuous % CHHP decomposition results for bulk metal hydroxide catalysts and silica-supported metal hydroxide catalysts. Example 21 (Table III) shows that very little thermal decomposition of CHHP occurred using silica under the conditions shown.

Examples 36–39 (Table V) give batch % t-butylhydroperoxide (t-BuOOH) decomposition results for titanosilicate catalysts prepared by sol-gel techniques and silica-supported Co and Nb catalysts. Analyses for % t-BuOOH decomposition were done by GC analysis on a DB-17 column as described above for analyses of % CHHP decomposition in Examples 13–21 (Table III).

Examples 40–43 (Table VI) give batch % cumenehydroperoxide (CumeneOOH) decomposition results for titanosilicate catalysts prepared by sol-gel techniques and silica-supported Co and Nb catalysts. Analyses for % CumeneOOH decomposition were done using a well known iodometric titration procedure, described in "Comprehensive Analytical Chemistry," Elsevier Publishing Company, New York, Eds. C. L. Wilson and D. W. Wilson, p. 756, 1960. Starting and product solutions of CumeneOOH in n-octane were analyzed by adding excess NaI/2-propanol solution, followed by heating to 70° C. for 15 minutes and titration with 0.1M $Na_2S_2O_3$ solution for amounts of $I_2$ liberated by CumeneOOH present.

TABLE I

| Ex. | Catalyst, g | Method of prep. | Approx. Wt. % CHHP | Reaction Temp, ° C. | Time. min | $\left(\dfrac{mmolCHHP}{gTCB}\right)$ initial | $\left(\dfrac{mmolCHHP}{gTCB}\right)$ final | % CHHP Decomp. |
|---|---|---|---|---|---|---|---|---|
| 1 | Sulf. $ZrO_x(OH)_{4-2x}$, 0.0051 | Exp. 2 | 1 | 115 | 10 | 49.8 | 17.1 | 65.6 |
| 2 | $ZrO_x(OH)_{4-2x}$, 0.0053 | Exp. 1 | 2 | 120 | 10 | 26.0 | 4.2 | 83.8 |
| 3 | $NbO_x(OH)_{5-2x}$, 0.0051 | Exp. 3 | 2 | 120 | 10 | 26.0 | 21.3 | 18.2 |
| 4 | $TiO_x(OH)_{4-2x}$, 0.0051 | Exp. 16 | 2 | 120 | 10 | 45.4 | 32.7 | 28.0 |

TABLE II

| Ex. | Catalyst, g wt. % Ti | Method of prep. | Approx. Wt. % CHHP | Calcin. Temp., ° C. | Reaction Temp, ° C. | Time, min | Wt. % (GC) CHHP initial | Wt. % (GC) CHHP final | % CHHP Decomp. |
|---|---|---|---|---|---|---|---|---|---|
| 5 | TiSiO, 0.0102, 1 | Exp. 8 | 2 | 500 | 125 | 5 | 2.02 | 1.26 | 37.8 |
| 6 | TiSiO, 0.0103, 5 | Exp. 8 | 2 | 500 | 125 | 5 | 2.02 | 0.98 | 51.5 |
| 7 | TiSiO, 0.0113, 10 | Exp. 8 | 2 | 300 | 125 | 5 | 1.70 | 0.92 | 45.9 |
| 8 | TiSiO, 0.0110, 10 | Exp. 8 | 2 | 500 | 125 | 5 | 1.70 | 0.60 | 64.7 |
| 9 | TiSiO, 0.0111, 25 | Exp. 8 | 2 | 300 | 125 | 5 | 1.70 | 1.56 | 8.0 |
| 10 | TiSiO, 0.0111, 25 | Exp. 8 | 2 | 500 | 125 | 5 | 1.70 | 1.50 | 11.8 |
| 11 | TiSiO, 0.0110, 6 | Exp. 9 | 2 | 600 | 125 | 5 | 1.94 | 0.25 | 86.9 |
| 12 | TiSiO, 0.0110, 6 | Exp. 9 | 2 | 600 | 125 | 5 | 1.94 | 0.42 | 78.5 |

TABLE III

| Ex. Catalyst, g | Method of prep. | Temp., ° C. | Time, hr | Wt. % (GC) CHHP initial | Wt. % (GC) CHHP final | % CHHP Decomp. |
|---|---|---|---|---|---|---|
| 13 ZrO$_x$(OH)$_{4-2x}$/SiO$_2$, 1.00 | Exp. 4 | 100 | 23 | 1.84 | 1.49 | 19.0 |
| | | | 24 | 1.91 | 1.77 | 7.3 |
| 14 ZrO$_x$(OH)$_{4-2x}$, 0.94 | Exp. 1 | 125 | 24 | 1.79 | 1.37 | 27.9 |
| | | | 48 | 1.79 | 1.49 | 17.2 |
| | | | 62 | 1.81 | 1.50 | 17.1 |
| 15 ZrO$_x$(OH)$_{4-2x}$/SiO$_2$, 1.02 | Exp. 4 | 125 | 24 | 1.16 | 1.08 | 6.9 |
| | | | 48 | 1.12 | 1.06 | 13.8 |
| | | | 72 | 1.20 | 0.76 | 36.7 |
| 16 TiO$_x$(OH)$_{4-2x}$, 1.01 | Exp. 16 | 100 | 23 | 1.86 | 1.83 | 1.6 |
| | | | 24 | 1.86 | 1.79 | 3.8 |
| 17 TiO$_x$(OH)$_{4-2x}$/SiO$_2$, 1.24 | Exp. 5 | 125 | 24 | 1.21 | 0.69 | 43.0 |
| | | | 48 | 1.22 | 0.58 | 52.5 |
| | | | 72 | 1.19 | 0.60 | 49.6 |
| 18 NbO$_x$(OH)$_{5-2x}$, 1.05 | Exp. 3 | 15 | 25 | 1.87 | 1.66 | 11.2 |
| | | | 48 | 1.91 | 1.70 | 11.0 |
| | | | 72 | 1.92 | 1.66 | 13.5 |
| 19 NbO$_x$(OH)$_{5-2x}$/SiO$_2$, 1.00 | Exp. 6 | 100 | 22 | 1.57 | 0.98 | 37.9 |
| | | | 23 | 1.64 | 1.26 | 23.2 |
| | | | 24 | 1.62 | 1.31 | 19.1 |
| 20 NbO$_x$(OH)$_{5-2x}$/SiO$_2$, 1.04 | Exp. 6 | 125 | 24 | 1.18 | 0.88 | 25.4 |
| | | | 28 | 1.25 | 0.99 | 20.8 |
| | | | 72 | 1.20 | 0.60 | 50.0 |
| 21 SiO$_2$, 1.08 | — | 100 | 4 | 1.95 | 1.89 | 3.1 |
| | | | 20 | 1.96 | 1.91 | 2.6 |

TABLE IV

| Ex. Catalyst, g | Method of prep. | Mol % Zr/Si | Approx. Wt. % CHHP | Temp., ° C. | Time, hr | Wt. % (GC) CHHP initial | Wt. % (GC) CHHP final | % CHHP Decomp. |
|---|---|---|---|---|---|---|---|---|
| 22 NbO$_x$(OH)$_{5-2x}$/C, 0.0102 | Exp. 17 | — | 2 | 125 | 5 | 6.28 | 3.89 | 38.0 |
| 23 HfO$_x$(OH)$_{4-2x}$/SiO$_2$, 0.0102 | Exp. 18 | — | 2 | 125 | 5 | 6.28 | 5.13 | 18.3 |
| 24 NbO$_x$(OH)$_{5-2x}$, 0.0114 | Exp. 12a | — | 2 | 125 | 5 | 1.96 | 0.40 | 79.7 |
| 25 NbO$_x$(OH)$_{5-2x}$, 0.0109 | Exp. 12b | — | 2 | 125 | 5 | 2.68 | 0.96 | 64.4 |
| 26 NbO$_x$(OH)$_{5-2x}$, 0.0110 | Exp. 13a | — | 2 | 125 | 5 | 2.68 | 0.75 | 72.0 |
| 27 NbO$_x$(OH)$_{5-2x}$, 0.0115 | Exp. 13b | — | 2 | 125 | 5 | 1.96 | 1.45 | 25.9 |
| 28 ZrSiO, 0.0110 | Exp. 11 | 33:67 | 2 | 125 | 5 | 1.96 | 0.66 | 66.1 |
| 29 ZrSiO, 0.0118 | Exp. 10 | 33:67 | 2 | 125 | 5 | 1.96 | 0.67 | 65.7 |
| 30 ZrSiO, 0.0111 | Exp. 11 | 50:50 | 2 | 125 | 5 | 2.68 | 1.58 | 41.0 |
| 31 ZrSiO, 0.0111 | Exp. 10 | 50:50 | 2 | 125 | 5 | 2.78 | 1.35 | 51.5 |
| 32 ZrSiO, 0.0115 | Exp. 11 | 67:33 | 2 | 125 | 5 | 1.96 | 1.10 | 43.7 |
| 33 ZrSiO, 0.0111 | Exp. 10 | 67:33 | 2 | 125 | 5 | 1.96 | 0.91 | 53.5 |
| 34 TiSiO, 0.0109 | Exp. 14 | — | 2 | 125 | 5 | 2.78 | 0.98 | 64.9 |
| 35 TiSiO, 0.0111 | Exp. 15 | — | 2 | 125 | 5 | 2.78 | 1.16 | 58.1 |

TABLE V

| Ex. Catalyst, g | Method of preparation | Approx. Wt. % tBuOOH | Reaction Temp., ° C. | Time, min | tBuOOH, Area % (TCB, Area %) initial | tBuOOH, Area % (TCB, Area %) final | % tBuOOH Decomp. |
|---|---|---|---|---|---|---|---|
| 36 TiSiO, 0.0100 | Exp. 9 | 0.70 | 125 | 5 | 0.136 | 0.132 | 2.9 |
| 37 TiSiO, 0.0100 | Exp. 8 | 0.70 | 125 | 5 | 0.136 | 0.123 | 9.6 |
| 38 Co/SiO$_2$, 0.0106 | — | 0.70 | 125 | 5 | 0.136 | 0.139 | 0 |
| 39 NbO/SiO$_2$, 0.0105 | Exp. 6 | 0.70 | 125 | 5 | 0.136 | 0.133 | 2.2 |

TABLE VI

| Ex. Catalyst, g | Method of preparation | Approx. Wt. % CumeneOOH | Reaction Temp., ° C. | Time, min | Molarity CumeneOOH initial | Molarity CumemeOOH, final | % CumeneOOH Decomp. |
|---|---|---|---|---|---|---|---|
| 40 TiSiO, 0.0103 | Exp. 9 | 1.13 | 125 | 5 | 2.7 | 0.62 | 77 |
| 41 TiSiO, 0.0106 | Exp. 8 | 1.13 | 125 | 5 | 2.7 | 0.53 | 80 |
| 42 Co/SiO$_2$, 0.0106 | — | 1.13 | 125 | 5 | 2.7 | 2.02 | 25 |
| 43 NbO/SiO$_2$, 0.0100 | Exp. 6 | 1.13 | 125 | 5 | 2.7 | 1.40 | 48 |

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

We claim:

1. An improved process for decomposing a hydroperoxide to form a decomposition reaction mixture containing a corresponding alcohol and ketone, the improvement comprising decomposing the hydroperoxide by contacting the hydroperoxide with a catalytic amount of a heterogeneous catalyst selected from the group consisting of Nb hydroxides or oxides.

2. The process according to claim 1 wherein the hydroperoxide is cyclohexylhydroperoxide.

3. The process according to claim I wherein the heterogenous catalyst is supported on a catalyst support selected from the group consisting of SiO$_2$, Al$_2$O$_3$, carbon and TiO$_2$.

4. The process according to claim 1 or 3 wherein the decomposition reaction temperature is from about 80° C. to about 170° C., and decomposition reaction pressure is from about 69 kPa to about 2760 kPa.

5. The process according to claim 4 wherein the reaction pressure is from about 276 kPa to about 1380 kPa.

6. The process according to claim 1 wherein the reaction mixture contains from about 0.5 to about 100 percent by weight cyclohexyl hydroperoxide.

7. The process according to claim 2 wherein the process is run in the presence of cyclohexane.

8. The process according to claim 1 or 3 wherein the process is run in the presence of oxygen.

9. The process according to claim 3 wherein the catalyst is supported on SiO$_2$.

10. The process according to claim 9 wherein the Nb hydroxide or oxide is from about 1 to about 25 wt. percent of the catalyst.

* * * * *